United States Patent [19]
Cortes et al.

[11] Patent Number: 5,522,988
[45] Date of Patent: Jun. 4, 1996

[54] ON-LINE COUPLED LIQUID AND GAS CHROMATOGRAPHY SYSTEM WITH AN INTERFACE CAPILLARY TUBE INTERPOSED BETWEEN A PAIR OF CAPILLARY CHROMATOGRAPHIC COLUMNS

[75] Inventors: Hernan J. Cortes; Curtis D. Pfeiffer, both of Midland, Mich.; Bruce E. Richter, Orem, Utah

[73] Assignee: The Dow Chemical Company, Midland, Mich.

[21] Appl. No.: 318,481

[22] Filed: Oct. 5, 1994

Related U.S. Application Data

[60] Continuation of Ser. No. 68,481, May 28, 1993, abandoned, which is a division of Ser. No. 982,266, Nov. 25, 1992, Pat. No. 5,236,593, which is a continuation of Ser. No. 576,533, Aug. 31, 1990, abandoned, which is a continuation of Ser. No. 457,203, Dec. 26, 1989, abandoned, which is a continuation of Ser. No. 348,354, May 5, 1989, abandoned, which is a continuation of Ser. No. 209,609, Jun. 21, 1988, abandoned, which is a continuation of Ser. No. 902,911, Aug. 29, 1986, abandoned, which is a continuation of Ser. No. 810,798, Dec. 18, 1985, abandoned, which is a continuation-in-part of Ser. No. 695,038, Jan. 25, 1985, abandoned.

[51] Int. Cl.$^6$ .................................................. B01D 15/08
[52] U.S. Cl. ......................... 210/198.2; 210/656; 96/104; 96/106
[58] Field of Search ..................... 210/635, 656, 210/198.2; 422/70; 436/161; 95/86, 87; 96/104, 106

[56] References Cited

U.S. PATENT DOCUMENTS

| | | | |
|---|---|---|---|
| 4,383,839 | 5/1983 | Sisti et al. | 55/67 |
| 4,483,773 | 1/1984 | Yang | 210/198.2 |
| 4,935,145 | 6/1990 | Cortes | 96/106 |

FOREIGN PATENT DOCUMENTS

| | | | |
|---|---|---|---|
| 38650 | 3/1984 | Japan | 210/198.2 |

OTHER PUBLICATIONS

K. Grob, Jr. et al., "Coupling Of High–Performance Liquid Chromatography With Capillary Gas Chromatography," J. of Chromatography, 295 (1984) 55–61.

K. Grob, Jr., "'Bank Broadening In Space' And The 'Retention Gap' In Capillary Gas Chromatography," J. of Chromatography, 237 (1982) 15–23.

K. Grob, Jr. et al., "Some Technical Aspects Of The Preparation Of A 'Retention Gap' In Capillary Gas Chromatography," J. of Chromatography, 244 (1982) 185–196.

Hernan Cortes et al., "Determination Of Trace Chlorinated Benzenes In Fuel Oil By On–Line Multidimensional Chromatography Using Packed–Capillary Liquid Chromatography And Capillary Gas Chromatography," J. of Chromatography, 349 (1985) 55–61.

H. J. Cortes et al., "On–Line Multidimensional Chromatography Using Packed Capillary Liquid Chromatography And Capillary Gas Chromatography," J. of High Resolution Chromatography & Chromatography Communications, (1985) vol. 8, 469–474.

(List continued on next page.)

*Primary Examiner*—Ernest G. Therkorn

[57] ABSTRACT

Apparatus and method for on-line coupled liquid chromatography and gas chromatography analysis. The system includes a high-volume, liquid vaporizing chamber, or interface capillary tube which allows injection of a substantial volume of sample-carrying eluent and concentrates bands, obviating adverse effects on the resolution or peak shape of the components of interest. The vaporizing chamber is interposed between a packed or wall-coated open tubular capillary liquid chromatographic column and a capillary gas chromatographic column. The capillary liquid chromatographic column permits the use of small volumes of eluent and reduced flow rates.

4 Claims, 5 Drawing Sheets

OTHER PUBLICATIONS

Hernan J. Cortes et al., "On–line Multidimensional Chromatography Using Micro HPLC and Capillary GC," Chromatography Forum, Nov.–Dec. (1986) 29–34.

Ronald E. Majors, "Multidimensional High Performance Liquid Chromatography," J. of Chromatographic Science, 18 (1980) 571–579.

J. A. Apffel et al., "Hydrocarbon Group–Type Analyses By On–Line Multi–Dimensional Chromatography," J. of Chromatography, 279 (1983) 139–144.

Mike's Laboratory Handbook of Chromatographic and Allied Methods, John Wiley & Sons, New York, 1979, pp. 539–540.

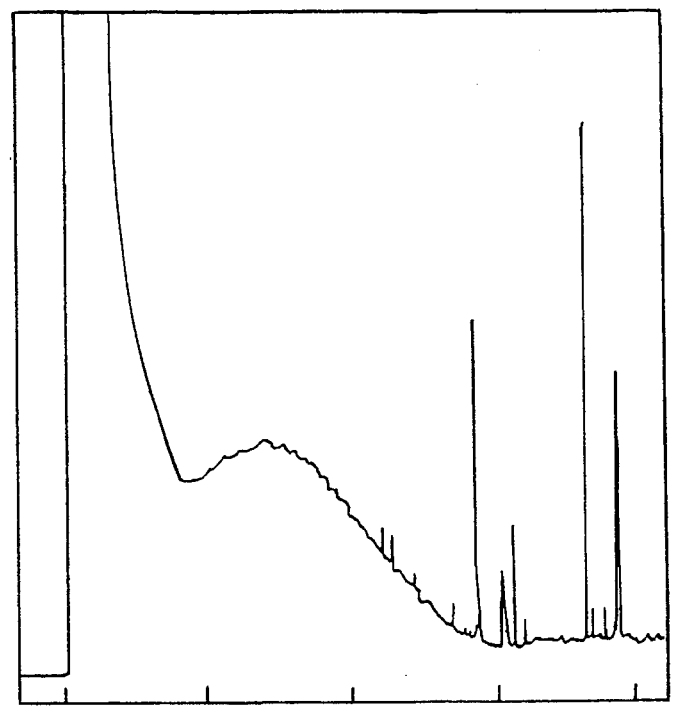
Fig. 6    TIME (MIN.)
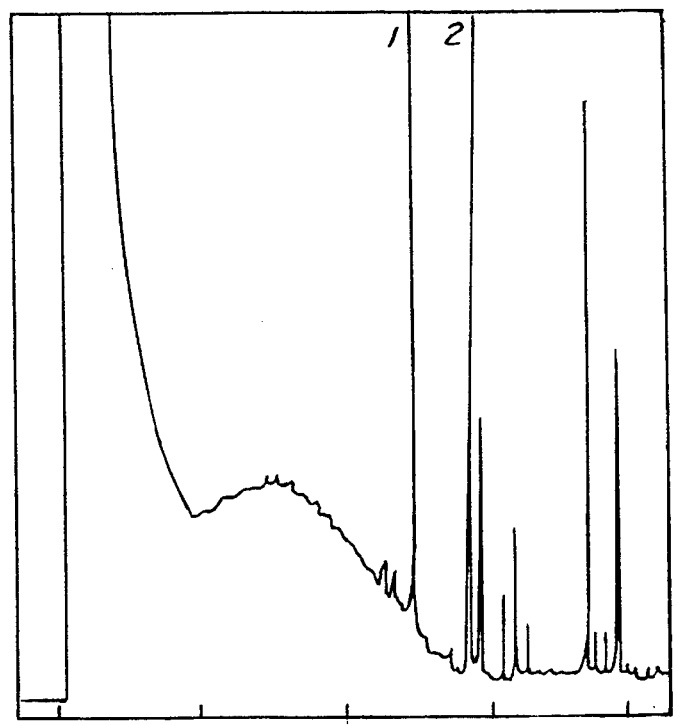
TIME (MIN)    Fig. 7

ON-LINE COUPLED LIQUID AND GAS CHROMATOGRAPHY SYSTEM WITH AN INTERFACE CAPILLARY TUBE INTERPOSED BETWEEN A PAIR OF CAPILLARY CHROMATOGRAPHIC COLUMNS

CROSS-REFERENCE TO RELATED APPLICATION

This is a continuation of application Ser. No. 08/068,481, filed May 28, 1993, now abandoned, which is a division of Ser. No. 07/982,266, filed Nov. 25, 1992, now U.S. Pat. No. 5,236,593, which is a continuation of Ser. No. 07/576,533, filed Aug. 31, 1990, now abandoned, which is a continuation of Ser. No. 07/457,203, filed Dec. 26, 1989, now abandoned, which is a continuation of Ser. No. 07/348,354, filed May 5, 1989, now abandoned, which is a continuation of Ser. No. 07/209,609, filed Jun. 21, 1988, now abandoned, which is a continuation of Ser. No. 06/902,911, filed Aug. 29, 1986, now abandoned, which is a continuation of Ser. No. 06/810,798, filed Dec. 18, 1985, now abandoned, which is a continuation-in-part of Ser. No. 06/695,038, filed Jan. 25, 1985, now abandoned,

BACKGROUND OF THE INVENTION

The present invention relates to apparatus and to a method of combining high-performance liquid chromatography with capillary gas chromatography. More particularly, the invention is directed to a method and apparatus for on-line coupling of liquid and gas chromatography columns in which there is direct, uninterrupted transfer of sample containing eluent from a liquid chromatographic analytical system to a gas chromatographic system.

In the general area of multidimensional chromatography, the introduction of selected fractions from a liquid chromatographic analytical system into a gas chromatographic system has been described. (K. Grob, Jr., et al., *J. Chromatography* 295, 55–61 [1984]). However, for the most part, such analyses have been carried out utilizing off-line techniques requiring collection and reinjection of the separate fractions, or by on-line procedures using conventional High Performance Liquid Chromatographic Columns (HPLC), where only a fraction of the separated peak could be introduced into the gas chromatographic equipment.

Efforts to increase the theoretical plate count and the speed of analysis in HPLC have been directed to reducing the particle size of the chromatographic support to a few microns, using open tubular columns analogous to capillary gas chromatography, and reducing column diameter in microbore and, more recently, using packed capillaries.

Among the advantages realized in utilizing packed capillaries for HPLC are the higher total efficiencies obtained by using longer columns, and the reduced eluent consumption. The latter feature permits the use of exotic solvents and the interfacing to detectors such as flame based and mass spectrometers.

The prior art does describe the use of conventional liquid chromatographic columns which have been coupled to gas chromatographic assemblies. However, the relatively fast flow rates (that is, the large volumes) used permitted only fractions of a peak to be introduced to the gas chromatographic assembly, or only the characterization of well resolved components, for example, one or two peaks in a mixture.

In spite of the widespread interest in conducting sequential, uninterrupted analyses utilizing the combination, in series, of a liquid chromatographic system followed by a gas chromatographic system, no completely satisfactory apparatus or technique has heretofore been achieved. It is, therefore, a principle aim of the present invention to provide an improved apparatus and method whereby the deficiencies and shortcomings of prior art techniques and equipment may be overcome.

Terms

A low flow rate liquid chromatography column means a column whose effective operating flow rate allows quantitative transfer of the component(s) of interest into a gas chromatography column through a capillary interface. Low flow rate liquid chromatography columns useful in the invention are generally capillary columns of an inner diameter of about 1 mm or less. Under careful flow conditions it is contemplated that larger columns can be employed for the purposes of the invention, e.g., liquid chromatography columns having an inner diameter of generally about 2 mm or less.

Quantitative transfer means introduction of the total component(s) of interest in the mixture eluting from the liquid chromatography column to the gas chromatography column.

Effective operating flow rates mean a flow rate not greater than that which would not allow effective trapping of the component(s) of interest at the head of the gas chromatography column.

Effective trapping means and is shown by not obtaining detrimental peak shapes, band broadening, or significantly diminished resolution which occurs because of excess eluent volume which carries the component(s) of interest from the interface into the gas chromatography column to an extent that it creates band broadening, diminished resolution, and/ or detrimental peak shape shown by excessive nongaussian peak character.

Detrimental peak shape, band broadening, and diminished resolution mean those conditions which produce unnecessary merged peaks, unnecessary nongaussian shapes of peaks which are difficult to quantitate, or peaks that are unnecessarily broadened to the point that quantitation at lower levels based, e.g., on peak height, becomes difficult or impossible.

SUMMARY OF THE INVENTION

The present invention pertains to an on-line multidimensional system in which a highly efficient packed liquid chromatography capillary column is coupled to a capillary gas chromatographic column. It is a very important feature of the invention that a high volume vaporizing chamber or conduit, or interface capillary tube (an uncoated fused silica tube) 2–20 meters long and having an inner diameter of up to about 1 mm is interposed mechanically between the output from the packed liquid capillary column and the input to the capillary gas chromatographic column, preferably a wall-coated open tubular type. The unique combination of the invention which includes a packed capillary liquid chromatographic column in conjunction with the vaporization tube or "high-volume" interface conduit makes it feasible to utilize relatively small volumes of eluent. In other embodiments of the invention the liquid chromatography column may be of the wall-coated, open tubular type.

It is an important advantage of the apparatus and method of the invention that the use of the preferred packed capillary liquid chromatographic column permits, in effect, a lower flow rate of sample through the analytical system.

Yet another important feature of the apparatus and method of the invention is that the retention chamber or interface capillary tube serves to effect an enhanced practical separation of the species of interest which are contained in the effluent from the liquid chromatography column.

A related feature of the method of the invention is that the interface capillary tube and the gas chromatography column are enclosed in an oven or heating device, the temperature of which is controllable to effect a sequential traverse, first of the eluent and then of the species of interest into the gas chromatography column.

It is a feature of the method of the invention that the solvent or eluent vaporizes in the interface capillary tube or vaporizing conduit and deposits the components of interest in the gas chromatography column where these species remain until the temperature is reset or programmed upwardly (after the eluent has passed through the column) whereupon the species of interest are concentrated and separated in the gas chromatography column, essentially without any interference from the original eluent.

In accordance with the practice of the technique and utilizing the apparatus of the present invention, the separation obtainable is markedly improved over what has heretofore been achievable utilizing conventional systems including prior on-line liquid chromatographic and gas chromatographic systems.

It is a practical feature of the improved method and apparatus of the invention that minor components in a complex matrix can be determined without extensive prior sample clean-up procedures.

A related feature of the invention is that determination of the presence of specific species of interest in a complex hydrocarbon matrix can be effectively carried out.

Other and further features, advantages and objects of the present invention will be evident from the following specification considered in conjunction with the drawings.

BRIEF DESCRIPTION OF THE DRAWINGS

FIG. 6 is a chromatogram of a selected portion of the liquid chromatographic column effluent known to contain the components of interest and introduced into the gas chromatographic section of the apparatus of the invention; and FIG. 7 is a chromatogram of the coal tar fraction shown in FIG. 6, but containing as well the polychlorinated biphenyls not included in chromatogram of FIG. 6.

DESCRIPTION OF PREFERRED EMBODIMENTS

The aims and objects of the invention are accomplished by providing an on-line coupled HPLC system and a gas chromatographic system employing a packed capillary liquid chromatographic column in conjunction with a liquid vaporizing chamber or interface capillary tube. The packed capillary liquid chromatographic column permits use of small volumes of eluent and of reduced flow rates. The liquid vaporizing chamber or conduit allows the injection of a substantial volume of sample-carrying eluent and concentrates the bands of the species of interest obviating adverse effects on the resolution or peak shape of the components of interest. The vaporizing conduit is interposed between the packed capillary liquid chromatography column and the capillary gas chromatography column.

Figure 1:
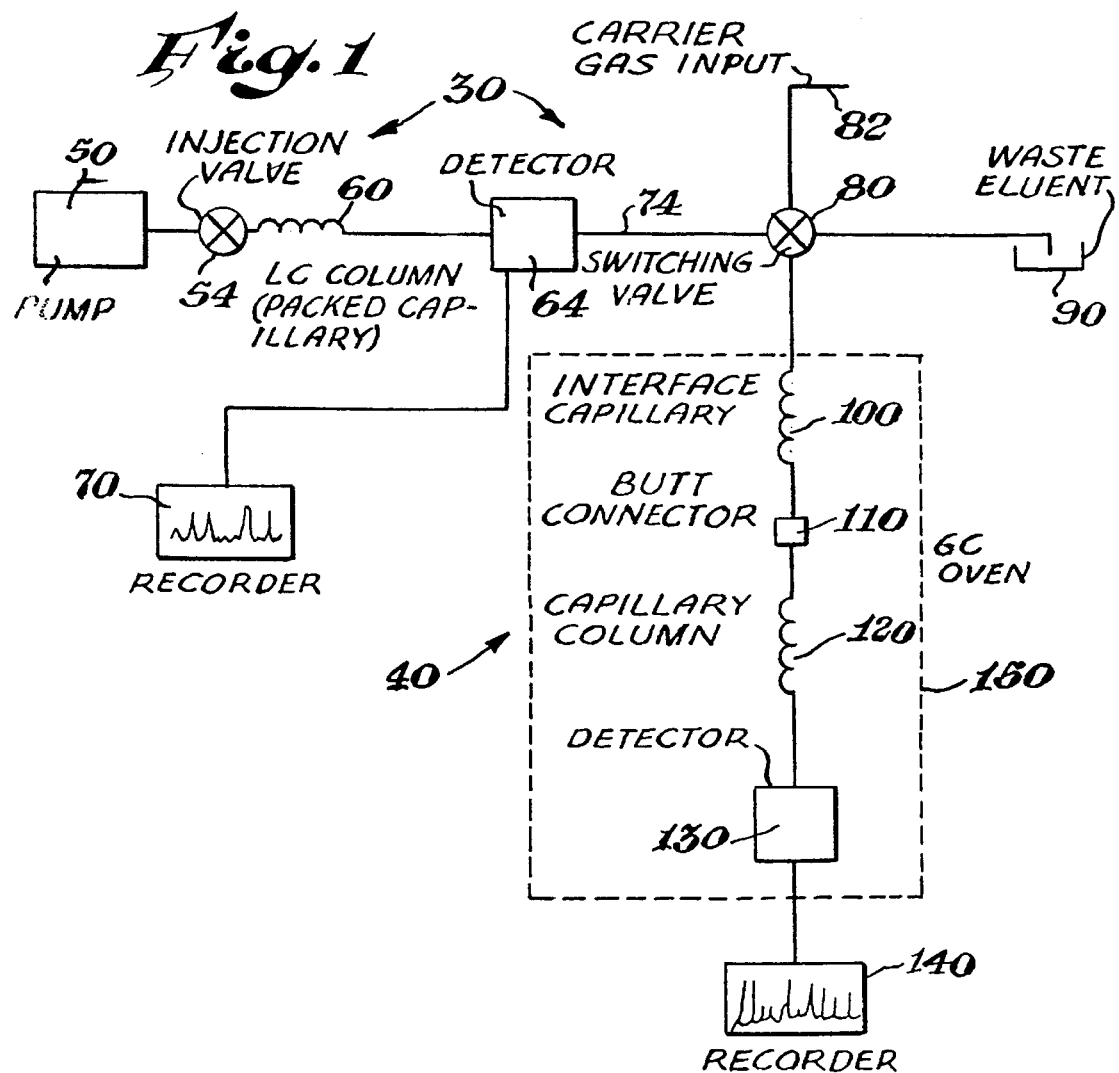
FIG. 1 is a schematic representation of an embodiment of the apparatus of the invention embodying the features thereof.

Referring now briefly to the drawings, and particularly to FIG. 1, there is shown for illustrative purposes and not in any limiting sense a block diagram indicating schematically the various component elements of the apparatus of the invention. As shown, the chromatography system 20 includes a liquid chromatography section 30 and a gas chromatography section 40. The liquid chromatography section 30 includes a pump 50 connected through a sample injection valve 54 to a packed capillary liquid chromatography column 60. The effluent from the column 60 is connected to a detector 64 which is connected in turn to recording apparatus 70. The detector 64 is connected through a suitable conduit 74 to a switching valve 80 from which an aliquot of the effluent from the detector is directed to the gas chromatography system 40, through which switching valve, a carrier stream 82 is also introduced into the system. A suitable line 84 is provided to direct excess effluent to waste 90.

Referring now to the gas chromatography section 40, there is indicated, schematically, an interface capillary tube, or vaporizing chamber 100 which receives the sample aliquot from the switching valve 80. The interface capillary gap or vaporizing chamber 100 is connected by means of a "butt" connector 110 to a gas chromatography capillary column 120, the latter being connected to a detector 130, and the detector to a recorder 140. With the exception of the recorder 140, the components of the gas chromatography system are housed within a temperature controlling oven 150.

The method of the invention, described briefly with reference to FIG. 1 will now be readily understood. A sample to be studied or investigated is introduced into the eluent flow system at the injection valve 54 and thereupon proceeds into the packed capillary column 60 of the invention. The packed capillary column makes possible the use of a relatively small volume of eluent and also facilitates a marked reduction in rate of flow or throughput. The effluent from the liquid packed capillary column is detected 64 and recorded 70 in a manner well known in the art.

However, rather than terminating the analytical procedure at this stage, the eluent containing the species of interest is directed from the detector, through a switching valve 80 to the interface capillary tube or vaporizing chamber 100, housed within an oven 150. In the interface capillary tube or vaporizing conduit 100, the eluent is transformed into vapor, and the temperature is so controlled that the eluent vapor passes through the butt connector 110 and through the gas capillary column 120 while the species of interest are "retained" in the capillary column 120. With the major portion of the eluent vaporized and discharged, the temperature of the oven is then reset (raised) to vaporize the species of interest which thereupon migrate through the gas capillary column and are separated and spaced in accordance with known techniques.

Finally, the species of interest are detected at the detector 130 and then recorded 140.

It will be appreciated that the apparatus and method described obviates the undesirable interference and related problems which a relatively substantial quantity of eluent pose in conducting analyses of the type described. The overall result of the method and apparatus of the invention is to achieve low flow rates allowing the loading of entire portions of the liquid column effluent into the gas chromatograph. The utilization of the interface capillary tube or vaporizing chamber, permits the injection of several microliters without the usual adverse effects upon the resolution or peak shape of the components of interest.

An additional advantageous feature of the apparatus and method of the invention is that the packed capillary liquid chromatography apparatus acts effectively as a highly efficient clean-up or chemical class fractionation stage prior to introduction of the sample into the gas chromatography equipment, thus significantly reducing sample preparation time for many applications. It has been effectively demonstrated that on-line multidimensional high resolution liquid chromatography-gas chromatography system of the invention is markedly superior to what is achievable using either liquid chromatography or gas chromatography alone. The techniques of the invention are particularly suited to the determination of trace levels of contaminants in extremely complex matrices. With the inclusion of valve actuators and auto samplers, the system of the invention becomes totally automated.

Details of the experimental procedure and the apparatus used are set forth in the paragraphs below.

EXPERIMENTAL

Liquid Chromatography

The liquid chromatography system used consisted of a Jasco Uvidec II detector equipped with a modified cell whose illuminated volume was calculated from the capillary diameter and the slit size. Wavelengths used were 254 nm for evaluation and 220 nm for sample analysis at 0.01 to 0.04 AUFS. Injections were made using a Valco model NI4W injection valve (Valco Inst., Houston, Tex., U.S.A.). Injection volumes varied between 60 and 200 nl. The solvent delivery system consisted of a Waters model M-45 pump equipped with a micro flow module, which allowed flow rates ranging from 1 µl/min. to 10 µl/min. The recorder used was a Sargent model xkr at 10 mv full scale.

The chromatography columns were constructed of fused silica capillaries with internal diameters of 100 µm, 250 µm (Spectran Corp., Sturbridge, Mass., U.S.A.) and 320 µm (Hewlett Packard Co., Avondale, Pa., U.S.A.). Column lengths ranged from 75 cm to 110 cm. The columns were packed at 6000 psi using a slurry technique.

Chromatographic supports used were Zorbax ODS, dp=7 µm (DuPont Inst., Wilmington, Del., U.S.A.), ODS-Hypersil, dp=5 µm (Shandon Southern Products, Ltd., Cheshire, England), and Spherisorb ODS, dp=10 µm (Phase Sep, Hauppauge, N.Y., U.S.A.).

Test mixtures used to evaluate the liquid chromatography system and to establish elution orders contained ammonium nitrate, phenol, methyl benzoate and acetophenone, prepared by dissolving about 100 mg of the organics and about 500 mg of ammonium nitrate, used as a marker to determine column void volumes, in 50 percent acetonitrile-water. The mobile phase used for evaluation purposes was 75 percent acetonitrile-water.

Gas Chromatography

The gas chromatography system consisted of a Hewlett Packard Model 5790 system equipped with a flame ionization detector.

Connection of the micro liquid chromatography equipment to the gas chromatography equipment was made with a switching valve 80 (Valco Model 4NI10WT) to keep the dead volume to a minimum. The valve was installed outside of the oven cabinet. An inlet section of capillary material free of stationary phase was connected between the switching valve 80 and the analytical column. This section, heretofore referred to as the vaporization conduit, interface capillary tube or the vaporizing chamber 100, as previously described, effectively focused the components of interest at the head of the gas chromatography column 120. A glass-lined stainless steel butt connector 110 (Scientific Glass Engineering, Inc., Austin, Tex, U.S.A.) was used to couple the interface capillary tube 100 to the analytical gas column 120 with essentially no "dead volume."

The analytical gas chromatography column used was a 30 meter, 0.25 mm I.D. column coated with Supelcowax 10 of 0.25 µm thickness (Supelco, Inc., Bellefonte, Pa, U.S.A.). The carrier gas was helium at a linear velocity of 68 cm/sec and nitrogen at 30 ml/min was used as the make-up gas for the flame ionization detector 130, operated at 265° C. The temperature of the oven 150 was maintained at 115° C. for 7 minutes, with a temperature program to 245° C. at 5° C. per minute.

A block diagram of the apparatus and its arrangement appears as FIG. 1.

RESULTS AND DISCUSSION

Effect and Role of Detector Cell Volume

The maximum detector cell volume for a packed capillary system that does not significantly contribute to system band broadening has been defined as:

$$Vd = 0.18\ L\, dp\, dc$$

where L=column length, dp=particle size and dc=capillary diameter. For a 75 cm column of 250 µm I.D. packed with 7 µm particles, the maximum detector volume would be 27 nl.

Effect of Column Diameter

Although column efficiency does not appear to depend upon column diameter in packed systems, fluctuations in packing density which may occur over the column diameter and temperature gradients generated due to viscous friction may contribute to band broadening which can be minimized by decreasing the column diameter.

Effect of Particle Size Diameter

The theoretical limit in terms of plate height of a packed column chromatography system has been described as being equivalent to two times the particle diameter. In the work conducted and reported herein, the plate heights range from 2.6 times particle diameter (10 µm) to 3.4 times particle diameter (5 µm) at the lower linear velocities which were employed.

EXAMPLE

A sample of coal tar was analyzed by micro HPLC as described hereinabove using a mobile phase of 100 percent acetonitrile.

Figure 2:
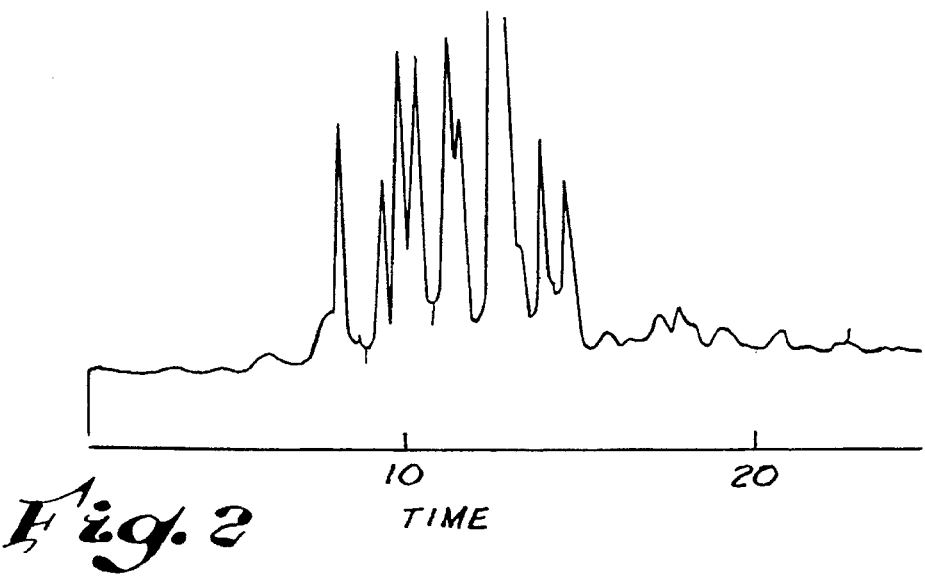
FIG. 2 is a chromatogram obtained in a conventional high performance liquid chromatographic system, indicating the type of resolution obtainable using a coal tar sample with 100 percent acetonitrile as the mobile phase.
Figure 3:
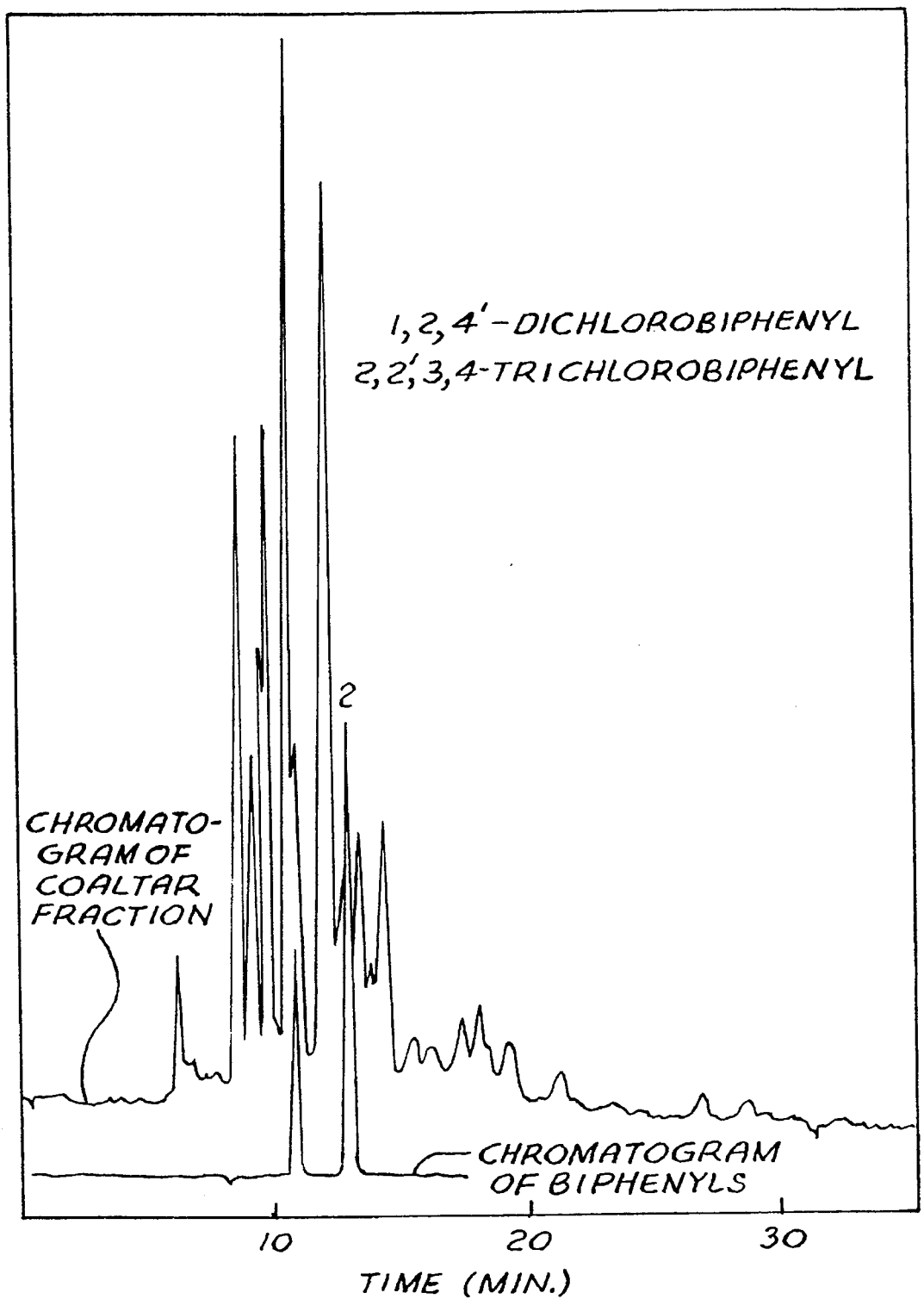
FIG. 3 is a chromatogram in which polychlorinated biphenyls have been elutriated with components of a coal tar mixture, and analyzed using the liquid chromatography apparatus and method of the present invention.

A chromatogram obtained utilizing a conventional HPLC system is included herein as FIG. 2. This chromatogram should be compared with that of FIG. 3 in which the system of the invention was employed.

Figure 4:
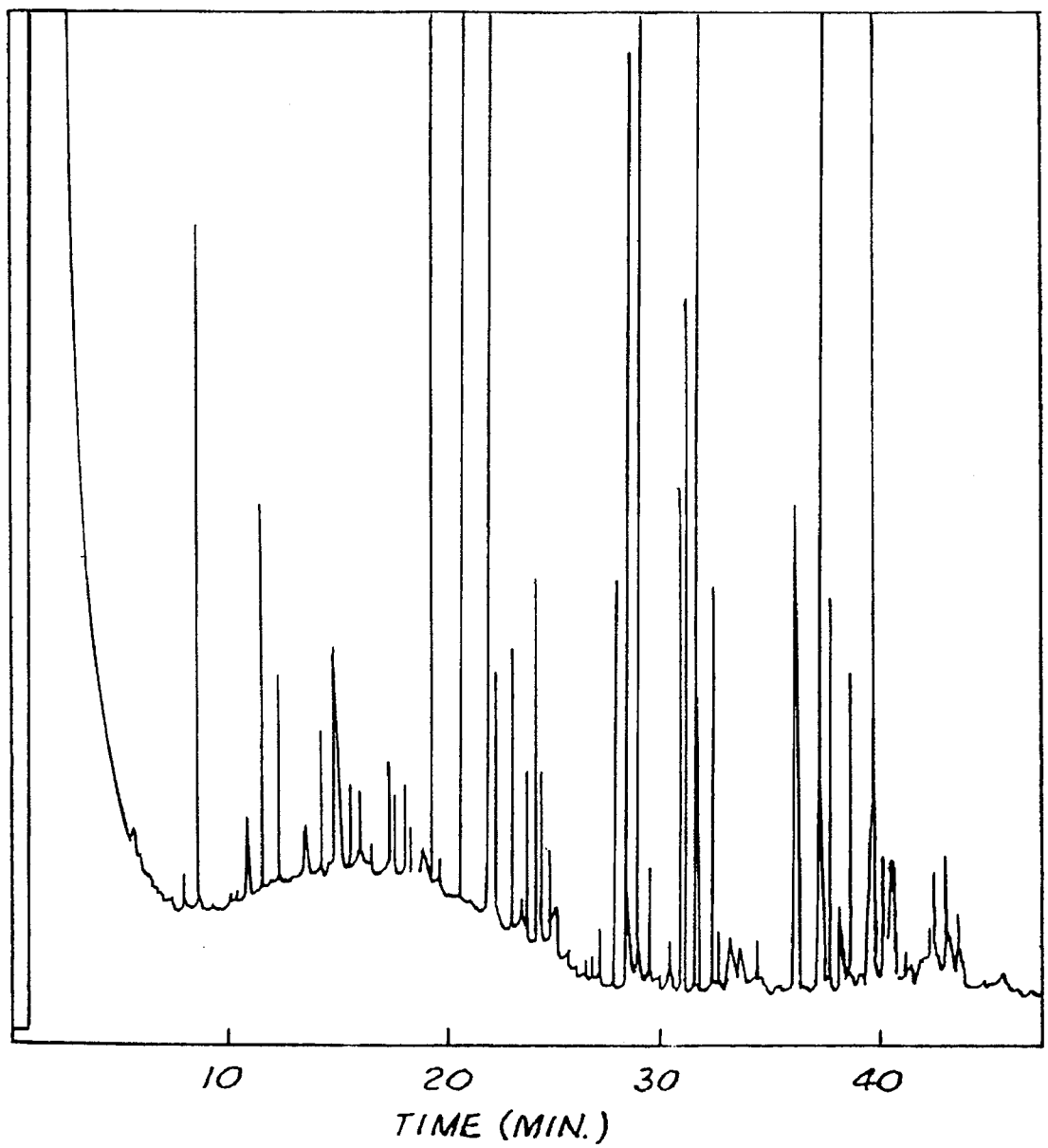
FIG. 4 represents a chromatogram obtained upon injection of a 10 microliter aliquot of a coal tar sample into the gas chromatograph port of the apparatus of the invention.
Figure 5:
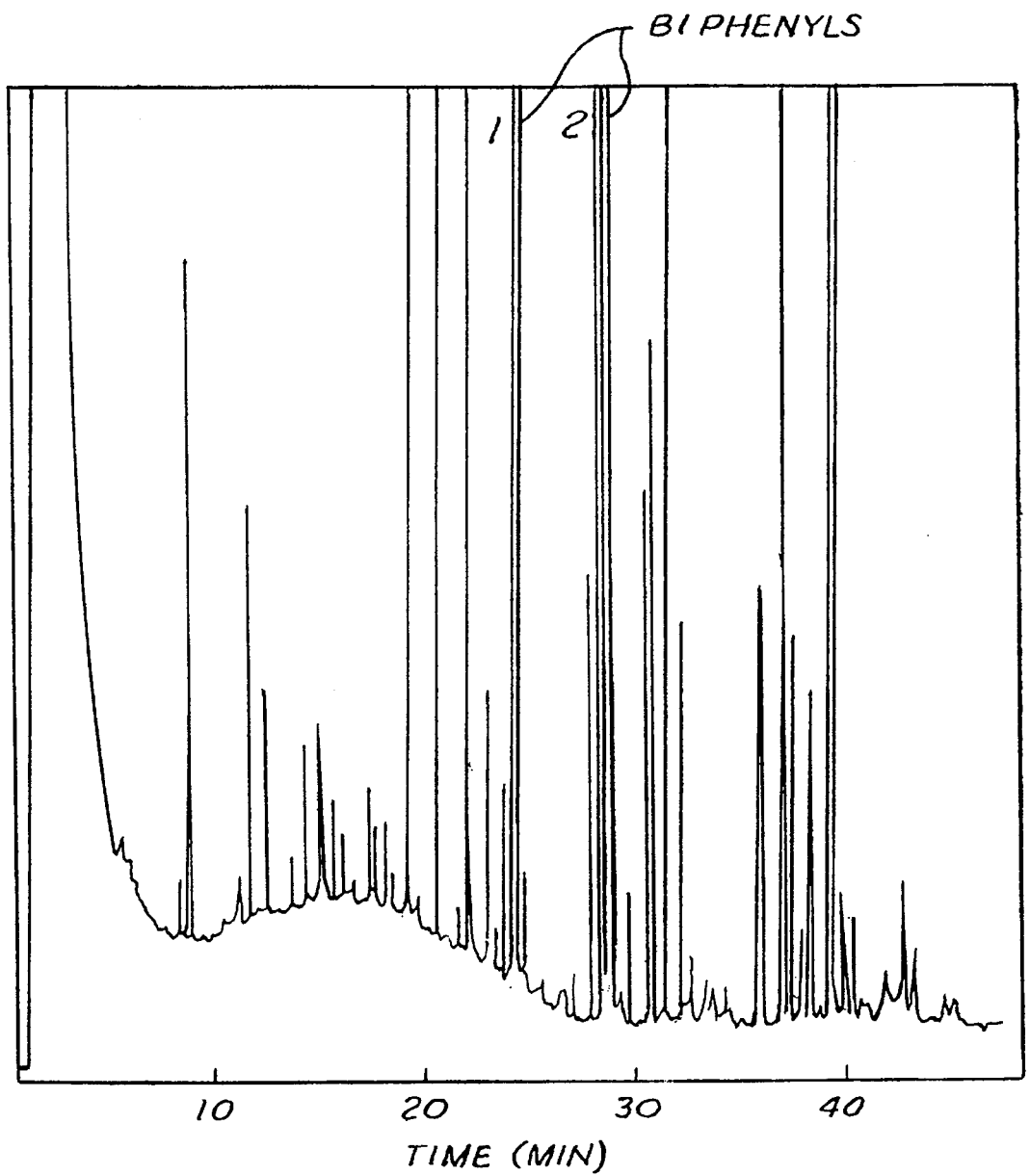
FIG. 5 is a chromatogram similar to that of FIG. 4 but of a sample which included polychlorinated biphenyls, and indicating that the polychlorinated biphenyls co-elute with various components of the coal tar mixture in the gas chromatography system.

A 10 μl injection of a coal tar sample and a coal tar sample containing the polychlorinated biphenyls (species of interest) produced the chromatograms depicted in FIGS. 4 and 5. As clearly indicated, the polychlorinated biphenyls elute with various components of the coal tar mixture in the gas chromatographic system.

The liquid chromatographic system was then connected to the switching valve 80 and the selected portion of the liquid chromatographic column effluent known to contain the components of interest was introduced into the gas chromatographic system. FIG. 6 represents a chromatogram using the combined liquid chromatographic and gas chromatographic system of the invention and carried out on a coal tar mixture that did not contain the polychlorinated biphenyls, while FIG. 7 represents a chromatogram of coal tar containing the polychlorinated biphenyls of interest.

The volume injected into the gas chromatography system was about 40 μl. The use of an interface capillary tube or vaporizing chamber, in accordance with the invention, allowed this quantity of polar eluent to be injected without any detrimental effects on the shapes of the peaks of interest. It is evident upon comparison of FIGS. 6 and 7 that the polychlorinated biphenyls of interest are effectively resolved from all other components in the coal tar matrix, indicating the superiority of the multidimensional approach of the invention to either liquid or to gas chromatography alone, and the superiority of the present invention over prior on-line combination systems.

It will be appreciated from the foregoing disclosure that there is herein provided a multidimensional chromatographic system for effectively coupling a packed capillary liquid chromatographic column to a capillary gas chromatographic column. The typical low flow rates of the micro liquid chromatographic system allows the loading of entire portions of the column effluent into the gas chromatographic system. The use of a vaporizing chamber or capillary tube allows injection of several microliters without adverse effects upon the resolution of peak shape of the components of interest.

While a particular preferred embodiment of the invention has been shown and described, it will be obvious to those skilled in the art that changes and modifications may be made without departing from the invention in its broader aspects. Therefore, the aim of the appended claims is to cover such changes and modifications as fall within the true spirit and scope of the invention.

What is claimed is:

1. Apparatus for introducing sample sequentially into a liquid chromatography capillary column means and a gas chromatography capillary column means, the apparatus comprising in cooperative combination:

(a) a liquid chromatography capillary column means, (b) a valve means for adding sample to the liquid chromatography capillary column means and a liquid chromatography pump means for adding liquid eluent to the liquid chromatography capillary column means whereby the sample is eluted through the liquid chromatography capillary column means and separated into components dispersed in the liquid effluent of the liquid chromatography capillary column means, (c) a gas chromatography capillary column means comprising a gas chromatography column having a stationary phase which is directly connected to a section of capillary material free of stationaty phase, (d) a liquid conduit means communicating between the liquid chromatography capillary column means and the section of capillary material free of stationary phase for adding liquid effluent containing sample originally added to the liquid chromatography column means to the gas chromatography capillary column means, (e) means for adding a gas to the section of capillary material free of stationary phase, (f) means for controllably heating the section of capillary material free of stationary phase, and (g) valving means for starting and stopping the flow of liquid effluent from the liquid chromatography capillary column means to the section of capillary material free of stationary phase and for starting and stopping the flow of gas to the inlet of the gas chromatography capillary columnb means such that when said valving means is stopping the flow of liquid effluent from the liquid capillary column means, said valving means is allowing the addition of gas to the section of capillary material free of stationary phase.

2. The apparatus of claim 1 including a liquid chromatography detector which communicates with said liquid conduit means for detecting components of sample dispersed in the effluent of the liquid chromatography column means.

3. The apparatus of claim 2 wherein the liquid capillary column means comprises a packed capillary column means or a wall-coated capillary column means, the liquid chromatography column means having a diameter of about 1 mm or less.

4. The apparatus of claim 1 wherein the liquid capillary column means comprises a packed capillary column means or a wall-coated capillary column means, the liquid chromatography column means having a diameter of about 1 mm or less.

\* \* \* \* \*